United States Patent
Wu

(10) Patent No.: US 8,257,971 B2
(45) Date of Patent: Sep. 4, 2012

(54) IN VITRO TUMOR ANGIOGENESIS MODEL

(75) Inventor: Min Wu, Carlise, MA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 193 days.

(21) Appl. No.: 12/697,700

(22) Filed: Feb. 1, 2010

(65) Prior Publication Data

US 2010/0136604 A1   Jun. 3, 2010

Related U.S. Application Data

(62) Division of application No. 11/381,763, filed on May 5, 2006, now Pat. No. 7,687,263.

(60) Provisional application No. 60/679,787, filed on May 11, 2005.

(51) Int. Cl.
   *C12N 5/00* (2006.01)
(52) U.S. Cl. ........................................ 435/325; 435/7.1
(58) Field of Classification Search ........................ None
   See application file for complete search history.

(56) References Cited

U.S. PATENT DOCUMENTS

| | | | |
|---|---|---|---|
| 6,197,534 | B1 | 3/2001 | Lakowicz et al. |
| 6,277,627 | B1 | 8/2001 | Hellinga |
| 2004/0214759 | A1 | 10/2004 | Alsobrook, II et al. |
| 2005/0064523 | A1 | 3/2005 | Wu |
| 2007/0092966 | A1 | 4/2007 | Wu |

FOREIGN PATENT DOCUMENTS

EP   1 506 998 B1   2/2005

OTHER PUBLICATIONS

Wakabayashi et al, Jpn J Cancer Res, 1995, 86:1189-1197.*
Chopra, et al., Three-Dimensional Endothelial-Tumor Epithelial Cell Interactions in Human Cervical Cancers, In vivo Cell. Dev. Biol.—Animal 33:432-442, Jun. 1997, 1997 Society for In Vitro Biology.
Miura, et al., Carcinosarcoma-induced endothelial cells tube formation through KDR/Flk-1 is blocked by TNP-470, Cancer Letters203 (2004) pp. 45-50.
Zhang, et al., Influence of breast carcinoma cells on normal endothelial cells: experimental study with co-culture system; pp. 1-3; www.ncbi.nlm.nih.gov/pubmed/16251075?dopt=Abstract; Mar. 19, 2009.
Gimi, et al., Noninvasive MRI of Endothelial Cell Response to Human Breast Cancer Cells, Nenoplasia, vol. 8 No. 3, Mar. 2006 pp. 207-213.
Abe, et al., induction of Vascular Endothelial Tubular Morphogenesis by Human Glioma Cells. A Model System For Tumor Angiogenesis, Journal of Clinical Investigation, 1993, pp. 54-61, vol. 92, No. 1.
Rao, Govind, Protein Engineered Glucose Sensor, 1998.
Lafleur et al., Endothelial tubulogenesis within fibrin gels specifically requires the activity of membrane-type-matrix metalloproteinases (MT-MMPs), Journal of Cell Science, Sep. 1, 2002, pp. 3427-3438, vol. 115, No. 17.
Nakagawa et al., Tubulogenesis by microvascular endothelial cells is mediated by vascular endothelial growth factor (VEGF) in renal cell carcinoma, British Journal of Urology, May 1997, pp. 681-687, vol. 79, No. 5.
Salins et al., A Novel Reagentless Sensing System for Measuring Glucose Based on the Galactose/Glucose-Binding Protein, Analytical Biochemistry, 2001, pp. 19-26, vol. 294, No. 1.
Tolosa et al., Glucose Sensor for Low-Cost Lifetime-Based Sensing Using a Genetically Engineered Protein, Analytical Biochemistry, 1999, pp. 114-120, vol. 267, No. 1.
Venetsanakos et al., Inducion by glioblastoma cells of tubulogenesis in telomerase-immortalized human microvascular endothelial cells, Feb. 1, 2002, Exp Cell Res, pp. 1-44.
Wenner et al., Genetically Designed Biosensing Systems for High-Throughput Screening of Pharmaceuticals, Clinical Diagnostics, and Environmental Monitoring, Advances in Fluorescence Sensing Technology V, 2001, pp. 59-70, vol. 4252.
Cai, et al., "Inhibition of angiogenic factor- and tumour-induced angiogenesis by gamma linolenic acid", Prostaglandins, Leukotrienes and Essential Fatty Acids, Jan. 1999, vol. 60 No. 1; pp. 21-29.
Gendaiiryo, "Co-Culture in vitro", Modern Medicine, 1994, vol. 26, No. 6, pp. 1843-1847.
Khodarev, et al.: "Tumour-endothelium interactions in co-culture: coordinated changes of gene expression profiles and phenotypic properties of endothelial cells", Journal of Cell Science 116 (6), (2003) pp. 1013-1022.
Khodarev, et al.: "Endothelial Cells Co-Cultured With Wild-Type And Dominant/Negative p53-Transfected Glioblastoma Cells Exhibit Differential Sensitivity to Radiation-Induced Apoptosis," Int. J. Cancer 109, (2004), pp. 214-219.
Hurst, et al.: "Properties of an Immortalised Vascular Endothelial/Glioma Cell Co-Culture Model of the Blood-Brain Barrier," Journal of Cellular Physiology, 167(1996) pp. 81-88.

* cited by examiner

*Primary Examiner* — Misook Yu
*Assistant Examiner* — Mark Halvorson
(74) *Attorney, Agent, or Firm* — Hoffmann & Baron, LLP

(57) ABSTRACT

Provided is a method of inducing tubulogenesis in normal endothelial cells comprising co-culturing the normal endothelial cells with tumor cells and forming tubules from the normal endothelial cells.

6 Claims, No Drawings

IN VITRO TUMOR ANGIOGENESIS MODEL

CROSS-REFERENCE TO RELATED APPLICATION

This application is a division of U.S. application Ser. No. 11/381,763, filed May 5, 2006, now allowed, which claims the benefit of U.S. Provisional Application No. 60/679,787, filed May 11, 2005, the entire contents of which are incorporated herein by reference.

FIELD OF THE INVENTION

The present invention relates to an in vitro tumor angiogenesis model. The present invention further relates to a method of inducing tubulogenesis in normal endothelial cells.

BACKGROUND OF THE INVENTION

Endothelial cells that form the lining of blood vessels are well known for their capacity to adjust their numbers and arrangement to suite local requirements. All tissues depend on a blood supply and the blood supply depends on endothelial cells. Blood vessels create an adaptable life support system in every region of the body. If not for endothelial cells extending and maintaining this network of blood vessels, tissue growth and repair would not be possible.

The largest blood vessels are arteries and veins, which have a thick tough outer wall of connective tissue and smooth muscle. The wall is lined by a thin single layer of endothelial cells, separated from the surrounding outer layers by a basal lamina. While the amounts of connective-tissue and smooth muscle in the vessel wall may vary according to the vessel's diameter and function, the endothelial lining is always present. In the smaller capillaries and sinusoids, the walls consist solely of endothelial cells and basal lamina. Thus, endothelial cells line the entire vascular system. Studies have shown that arteries and veins develop from small vessels constructed solely of endothelial cells and a basal lamina, connective tissue and smooth muscle being added later where required upon signals from the endothelial cells.

Throughout the vascular system endothelial cells retain a capacity for cell division and movement. This is important in repair and maintenance of the vascular system. For example, if a part of the wall of a blood vessel is damaged and loses endothelial cells, neighboring endothelial cells will proliferate and migrate in to cover the exposed surface. Newly formed endothelial cells have also been known to cover the inner surface of plastic tubing used by surgeons to replace damaged blood vessels.

Endothelial cells not only repair damaged blood vessels, they also create new blood vessels. Endothelial cells do this in embryonic tissues to support growth, in normal adult tissue for repair and maintenance, and in damaged tissue to support repair. This process is called angiogenesis.

Angiogenesis is a critical component in embryonic development, tissue growth, tissue remodeling, and a number of pathologies. Angiogenesis results in the formation of new blood vessels. During angiogenesis, endothelial cells, which exist in a quiescent state as part of an existing blood vessel, grow and enter a migratory, proliferative state. This migratory, proliferative state is eventually resolved when the cells differentiate into capillary tubes and return to the quiescent state as part of a functional new blood vessel. Angiogenesis is orchestrated by a complex network of multiple macromolecular interactions.

Angiogenesis is regulated in both normal and malignant tissues by the balance of angiogenic stimuli and angiogenic inhibitors that are produced in the target tissue and at distant sites. Vascular endothelial growth factor-A (VEGF, also known as vascular permeability factor, VPF) is a primary stimulant of angiogenesis. VEGF is a multifunctional cytokine that is induced by hypoxia and oncogenic mutations and can be produced by a wide variety of tissues.

Angiogenesis is stimulated and harnessed by some neoplasms (e.g., tumors) to increase nutrient uptake. However, in contrast to normal angiogenesis, which leads to anastomoses (i.e., vessel connections) and capillary maturation, angiogenesis associated with neoplasia is typically a continuous process where vessel maturation is imperfect. Endothelial cells are activated by nearby neoplastic cells to secrete not only VEGF which stimulates angiogenesis, but also matrix metalloproteases (MMP) which degrade the surrounding extracellular matrix. The endothelial cells then invade the extracellular matrix where they proliferate, migrate, and organize to form new blood vessels, which support neoplasm growth and survival.

The newly vascularized neoplasm continues to grow, leading to further nutrient deprivation and chronic pro-angiogenic signaling. The vasculature of neoplasms is characterized by the presence of structural irregularities (lacunae) and a low rate of formation of inter-vessel connections. This incomplete vasculature is inefficient, such that often tumors require continuous angiogenesis to sustain themselves. Such imperfect vasculature is also believed to promote the shedding of neoplastic cells into the systemic circulation. Hence, the angiogenic potential of a neoplasm correlates with metastatic potential. As a significant proportion of neoplasms are dependent on continued angiogenesis, inhibition of angiogenesis blocks neoplasm growth which often leads to complete necrosis of the neoplasm.

Glial cells including astrocytes comprise a large proportion of the total cell population in the central nervous system. Unlike neurons, glial cells retain the ability to proliferate postnatally, and some glial cells still proliferate in the adult or aged brain. Uncontrolled glial proliferation can lead to aggressive primary intracranial tumors. Such tumors vary widely in morphology and behavior, and, according to the 1993 World Health Organization classification schema, can be separated into three subsets. Astrocytomas, the lowest grade tumors, are generally well-differentiated and tend to grow slowly. Anaplastic astrocytomas are characterized by increased cellularity, nuclear pleomorphism (ability to assume different forms), and increased mitotic activity. They are intermediate grade tumors and show a tendency to progress to a more aggressive grade. Glioblastoma cells are considered the most aggressive, with poorly differentiated cells, vascular proliferation, and necrosis. Glioblastoma U251 is a malignant cell line derived from the human glial cells.

The angiogenic effects of glioblastoma cells and other solid tumor cells in the presence of in vivo matrix effects and other in vivo ancillary factors, do not predict in vitro effectiveness in inducing primary endothelial cells in culture to grow, and more particularly do not predict in vitro effectiveness in inducing primary endothelial cells in culture to form tubules. The effectiveness of very low numbers of tumor cells to induce this effect is still more unexpected.

Non-normal, i.e., immortalized endothelial cells have been reported to form tubular structures in culture in the presence of glioblastoma cells. But the growth of these kinds of cells can be expected to differ considerably from normal cells, so the induction of tubules in normal cells could not be reliably predicted from this earlier work.

Thus, there is a need to induce angiogenic endothelial cells to better enable collection of angiogenic endothelial cells for such purposes as angiogenic assay kits and in the study of endothelial cells, particularly the functions and permeability of the endothelial cell barrier. Further, such cells have potential therapeutic uses.

SUMMARY OF THE INVENTION

The present invention provides a method of inducing tubulogenesis in normal endothelial cells. The method includes co-culturing tumor cells with normal endothelial cells and forming tubules from the normal endothelial cells. In some embodiments, the tumor cells may include, but are not limited to, glioblastoma cells, such as glioblastoma U251, or engineered or selected derivatives of glioblastoma cells (e.g., transfected with VEGF). The normal endothelial cells are defined herein as endothelial cells that have not been immortalized. These may include, but are not limited to, human dermal microvascular endothelial cells, human pulmonary microvascular endothelial cells or human umbilical vein endothelial cells.

In some embodiments, the step of co-culturing the tumor cells and normal endothelial cells includes incubating the endothelial cells and tumor cells in an endothelial cell culture medium for at least 1 day and forming tubules from the incubated endothelial cells.

The present invention further provides a method of preparing angiogenic normal endothelial cells. The method includes co-culturing normal endothelial cells with tumor cells; and forming tubules from the normal endothelial cells. The method also includes selectively collecting the tubules, wherein the tubules include angiogenic normal endothelial cells. The "angiogenic normal endothelial cells" may be referred to interchangeably herein as "selected normal endothelial cells".

Further provided is a method of identifying bioactive agents. The identified bioactive agents may reduce or enhance tubulogenesis, for example. The method includes co-culturing normal endothelial cells with tumor cells, thereby forming tubules from the normal endothelial cells. The method further includes contacting the normal endothelial cells with a prospective bioactive agent; and monitoring for changes in tubule formation resulting from the presence of the bioactive agent. The changes are monitored relative to a control, i.e., the same method conducted in the absence of the prospective bioactive agent.

DETAILED DESCRIPTION OF THE INVENTION

For simplicity and illustrative purposes, the principles of the present invention are described by referring to various exemplary embodiments thereof. Although the preferred embodiments of the invention are particularly disclosed herein, one of ordinary skill in the art will readily recognize that the same principles are equally applicable to, and can be implicated in other compositions and methods, and that any such variation would be within such modifications that do not part from the scope of the present invention. Before explaining the disclosed embodiments of the present invention in detail, it is to be understood that the invention is not limited in its application to the details of any particular embodiment shown, since of course the invention is capable of other embodiments. The terminology used herein is for the purpose of description and not of limitation. Further, although certain methods are described with reference to certain steps that are presented herein in certain order, in many instances, these steps may be performed in any order as may be appreciated by one skilled in the art, and the methods are not limited to the particular arrangement of steps disclosed herein.

Endothelial cells are the cells that make up the inside of blood vessels. The term "normal endothelial cells" as used herein are endothelial cells that have not been immortalized. The term is meant to include human endothelial cells, as well as other mammalian and other vertebrate endothelial cells. Normal endothelial cells include, but are not limited to, human dermal microvascular endothelial cells and human pulmonary microvascular endothelial cells (HMVEC) and human umbilical vein endothelial cells (HUVEC). These and other normal endothelial cells are commercially available, for example, from BD Biosciences, a business segment of Becton, Dickinson & Co. (San Jose, Calif.), Cascade Biologies, Inc. (Portland, Oreg.) and Cambrex Corporation (East Rutherford, N.J.). Mammalian cells, particularly human cells, are preferred. Selected normal endothelial cells comprise normal endothelial cells that are believed to have relatively high angiogenesis potential. These are alternatively referred to herein as angiogenic normal endothelial cells.

The method of inducing tubulogenesis involves co-culturing tumor cells with normal endothelial cells. In a preferred embodiment, the method includes co-culturing tumor cells with endothelial cells, forming tubules from the normal endothelial cells and selectively collecting the formed tubules. The formed tubules include angiogenic normal endothelial cells. In one example, the tubules may be bound tentatively to the bottom surface of a well of a multi-well plate. The cell medium above the bound tubules in the well may include normal endothelial cells that have not differentiated into tubules. Therefore, in some embodiments, the cell medium in the well is removed and the bound tubules are gently washed and then dislodged (e.g., mechanically) in a suitable volume of fresh cell medium. In some embodiments, angiogenic endothelial cells selectively collected in this way may be employed in angiogenesis assays, if desired.

In a preferred embodiment, the co-culturing is performed at an endothelial cell to tumor cell ratio of approximately 5:1 or more, or 50:1 or more.

In an embodiment of the present invention, endothelial cells and tumor cells, such as glioblastoma U251, are harvested and then suspended in an endothelial cell culture medium. The desired number of each cell type is added to a microwell and incubated. In a preferred embodiment, the incubation occurs for more than 1 day. In a more preferred embodiment, the incubation lasts for more than 2 days. In a preferred embodiment, incubation occurs in a 5% $CO_2$ incubator at 37 degrees Celsius.

Tumor cells that are suitable for use in the method are those that are known to induce angiogenesis. For example, tumor cells known to induce angiogenesis include those from a wide variety of solid tumors, such as non-small cell lung cancer, prostate cancer, breast cancer, gastric cancer, and tumors of the head and neck. Specific examples of angiogenic tumor cell lines from these types of solid tumors are well known in the art, and may be obtained, for example, from American Type Culture Collection (ATCC, Manassas, Va.). In some preferred embodiments, the tumor cells are glioblastoma cells, such as glioblastoma U251. In general, suitable tumor cells release pro-angiogenic factors as signals for angiogenesis. Such pro-angiogenic factors include, for example, vascular endothelial growth factor (VEGF) acidic fibroblast growth factor, angiogenin, basic fibroblast growth factor (bFGF), epidermal growth factor, granulocyte colony stimulating factor, hepactocyte growth factor, interleukin-8, placental growth factor, platelet-derived growth factor, endothelial growth factor, scatter factor, transforming growth factor α and tumor necrosis factor α. Of these, two proteins appear to be the most important for sustaining tumor growth: VEFG and bFGF. VEGF and bFGF are produced by many types of cancer cells and by certain types of normal cells, too.

In some embodiments, tumor cell derivatives are employed in the present invention. For example, useful tumor cell derivatives include, but are not limited to, those transfected with one or more of the pro-angiogenic factors described above, particularly VEGF and/or bFGF. In some embodiments, the tumor cells are engineered or selected derivatives of glioblastoma cells, such as glioblastoma U251 cells transfected with VEGF.

The method of inducing tubulogenesis can be incorporated into a method of identifying bioactive agents by contacting prospective bioactive agents with the endothelial cells at some time relevant to modulating tubule formation. This time frame can be readily determined experimentally. Such time frame can be before the endothelial cells are co-cultured with tumor cells, or during the co-culturing. Bioactive agents that reduce tubulogenesis are candidate bioactive agents for disrupting blood vessel formation (angiogenesis) sought to be induced by tumor cells. Bioactive agents that stimulate tubulogenesis are candidate bioactive agents to increase vascularization in tissue damaged by ischemic events, in tissue whose vascularization has been damaged by environmental factors such as smoking, and in and aged-related blindness. Tubulogenesis can be most simply monitored visually. However, tubule formation can be assessed quantitatively, if desired. For example, following tubulogenesis, the assays may be stained with Calcein AM, and images may be acquired and total tube length measured using an image analyzer (e.g., using MetaMorph from Universal Imaging Corporation). Tubulogenesis can also be monitored by assaying the levels of molecules that function as surrogate markers for tubulogenesis. Such methods of monitoring tubulogenesis are known in the art.

A bioactive agent is a substance that can act on a cell, tissue, organ or organism to create a change in the functioning of the cell, organ or organism. The prospective bioactive agent may be a chemical, such as a pharmaceutical agent. Other prospective bioactive agents include, but are not limited to, insecticides, herbicides, proteins, (e.g., growth factors and cytokines), peptides, etc.

A tubule formation altering effective amount of a bioactive agent is an amount effective to change the rate (to faster or slower), degree (greater or lesser) or morphology of tubule formation, or to change (upwards or downwards) another measure of tubulogenesis. The change is measured relative to a control tubule formation assay where the bioactive agent is not present.

EXAMPLE

Two types of primary human endothelial cells, HUVEC and HMVEC were each mixed at a ratio of 100:1 with tumor cell U251. The cells were seeded in 6-well plates at a density of $1\times10^6$/well. The co-cultures were incubated in endothelial cell medium EGM-2 MV (Cambrex, Walkersville, Md.) in a 37° C./5% $CO_2$ incubator and the medium was replaced every two days until day 11. Tube formation was visually observed on and after day 7 in both co-cultures.

Alternatively, tube formation is assessed after at least one day of incubating the co-cultures at 37° C./5% $CO_2$ by staining with Calcein AM. Images are thereafter acquired using a 2× objective lens and total tube length is measured using MetaMorph (Universal Imaging Corporation).

As described above, in some embodiments, the assays described in the present example are used to identify bioactive agents that inhibit or stimulate tubulogenesis. For example, normal endothelial cells, such as HUVEC and HMVEC, may be contacted with different amounts of a prospective bioactive agent before the normal endothelial cells are co-cultured with the tumor cells, and changes in tubule formation resulting from the presence of the bioactive agent may be monitored. Alternatively, different amounts of a prospective bioactive agent may be contacted with the normal endothelial cells during the co-culturing step, and changes in the tubule formation resulting from the presence of the bioactive agent may be monitored.

While the invention has been described with an emphasis on particular embodiments thereof, those skilled in the art may make various modifications to the described embodiments of the invention without departing from the scope of the invention. Although the invention has been described and disclosed in various terms and certain embodiments, the scope of the invention is not intended to be, nor should it be deemed to be, limited thereby and such other modifications or embodiments as may be suggested by the teachings herein are particularly reserved, especially as they fall within the breadth and scope of the claims here appended. Those skilled in the art will recognize that these and other variations are possible within the scope of the invention as defined in the following claims and their equivalents.

What is claimed is:

1. A method of identifying bioactive agents comprising:
   a) mixing and co-culturing normal endothelial cells with tumor cells, thereby forming tubules from the normal endothelial cells;
   b) contacting the normal endothelial cells with a prospective bioactive agent; and
   c) monitoring for changes in tubule formation resulting from the presence of the bioactive agent,
   wherein the normal endothelial cells are human endothelial cells that have not been immortalized and wherein the ratio of human endothelial cells to tumor cells is at least 5:1 wherein the tumor cells are glioblastoma cells.

2. The method of claim 1, wherein the normal endothelial cells are selected from the group consisting of human dermal microvascular endothelial cells, human pulmonary microvascular endothelial cells and human umbilical vein endothelial cells.

3. The method of claim 1, wherein the contacting step is performed during the co-culturing step.

4. The method of claim 1, wherein the contacting step is performed prior to the co-culturing step.

5. The method of claim 1, wherein the step of co-culturing comprises: incubating the normal endothelial cells and tumor cells in an endothelial cell culture medium for at least 1 day; and, forming tubules from the incubated endothelial cells.

6. The method of claim 1, wherein the glioblastoma cells comprise glioblastoma U251.

* * * * *